United States Patent
DeSantis et al.

[11] Patent Number: 5,817,033
[45] Date of Patent: Oct. 6, 1998

[54] NEEDLE CORE BIOPSY DEVICE

[76] Inventors: Stephen A. DeSantis, 23802 Inverness Pl., Laguna Niguel, Calif. 92677; Norman S. Gordon, 21 Snowapple, Irvine, Calif. 92714; Robert P. Cooper, 19332 Via De La Cielo, Yorba Linda, Calif. 92680

[21] Appl. No.: 658,487

[22] Filed: Jun. 10, 1996

Related U.S. Application Data

[63] Continuation-in-part of Ser. No. 417,750, Apr. 6, 1995, Pat. No. 5,560,373, which is a continuation-in-part of Ser. No. 331,283, Oct. 27, 1994, Pat. No. 5,469,860, which is a continuation-in-part of Ser. No. 225,594, Apr. 11, 1994, Pat. No. 5,511,556.

[51] Int. Cl.$^6$ .................................................... A61B 17/32
[52] U.S. Cl. .................... 600/562; 600/564; 600/565; 600/566; 600/567; 606/167; 606/170
[58] Field of Search .................... 128/749, 750, 128/751, 752, 753, 754, 759; 606/167, 170; 600/562, 564, 565, 566; 60/567

[56] References Cited

U.S. PATENT DOCUMENTS

| | | |
|---|---|---|
| Re. 34,056 | 9/1992 | Lindgren et al. . |
| 2,472,116 | 6/1949 | Maynes . |
| 2,660,342 | 11/1953 | Ruf . |
| 2,735,427 | 2/1956 | Sullivan . |
| 2,863,452 | 12/1958 | Ogle, Sr. . |
| 2,892,457 | 6/1959 | Sturtz . |
| 3,477,423 | 11/1969 | Griffith . |
| 3,517,668 | 6/1970 | Brickson . |
| 3,561,429 | 2/1971 | Jewett . |
| 3,819,091 | 6/1974 | Hollender . |
| 3,844,272 | 10/1974 | Banko . |
| 3,905,365 | 9/1975 | Colombo . |
| 4,461,305 | 7/1984 | Cibley . |
| 4,594,073 | 6/1986 | Stine . |
| 4,605,011 | 8/1986 | Naslund . |
| 4,708,147 | 11/1987 | Haaga . |
| 4,711,250 | 12/1987 | Gilbaugh, Jr. et al. . |
| 4,776,346 | 10/1988 | Beraha et al. . |
| 4,776,840 | 10/1988 | Freitas . |
| 4,781,700 | 11/1988 | Vicario . |
| 4,893,635 | 1/1990 | de Groot et al. . |
| 4,907,598 | 3/1990 | Bauer . |
| 4,950,265 | 8/1990 | Taylor . |
| 4,982,739 | 1/1991 | Hemstreet et al. . |
| 5,115,816 | 5/1992 | Lee . |
| 5,159,933 | 11/1992 | Hut . |
| 5,183,052 | 2/1993 | Terwilliger . |
| 5,213,110 | 5/1993 | Kedem et al. . |
| 5,220,926 | 6/1993 | Jones . |
| 5,224,470 | 7/1993 | Schnepp-Pesch et al. . |
| 5,241,969 | 9/1993 | Carson et al. . |
| 5,246,011 | 9/1993 | Caillouette . |
| 5,249,582 | 10/1993 | Taylor . |
| 5,469,860 | 11/1995 | De Santis . |
| 5,511,556 | 4/1996 | De Santis . |

*Primary Examiner*—Mickey Yu
*Assistant Examiner*—Dinh X. Nguyen
*Attorney, Agent, or Firm*—Stetina Brunda Garred & Brucker

[57] ABSTRACT

A needle biopsy device has a suction source, an inner cannula, and an outer cannula. The inner cannula has a biopsy reservoir formed proximate the distal end thereof and also has a lumen formed therein. The lumen provides fluid communication from the suction source to the biopsy reservoir. The outer cannula is slidably disposed about the inner cannula and has a cutter formed at the distal end thereof. The outer cannula has a distal position wherein it substantially covers the biopsy reservoir and has a proximate position wherein the biopsy reservoir is substantially exposed. An actuating mechanism moves the outer cannula from the distal position to the proximate position thereof, facilitates the application of suction from the suction source to the biopsy reservoir and moves the outer cannula from the proximate position to the distal position thereof. Moving the outer cannula from the distal position to the proximate position thereof and creating suction that the biopsy reservoir causes a tissue sample to be pulled into the biopsy reservoir. Moving the outer cannula from the proximal position to the distal position thereof causes the cutter to cut the tissue sample from surrounding tissue and also captures the tissue sample within the biopsy reservoir.

22 Claims, 3 Drawing Sheets

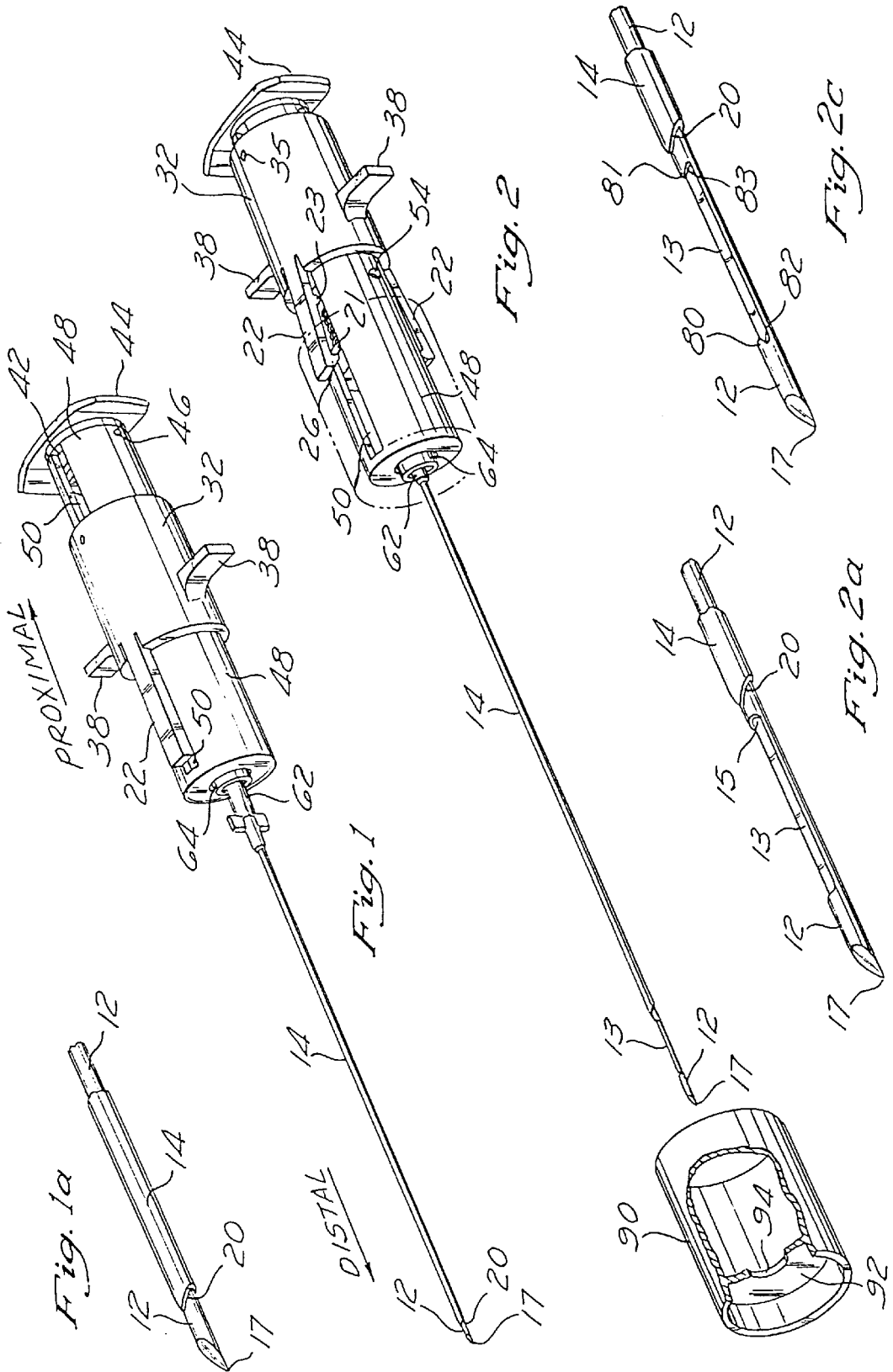

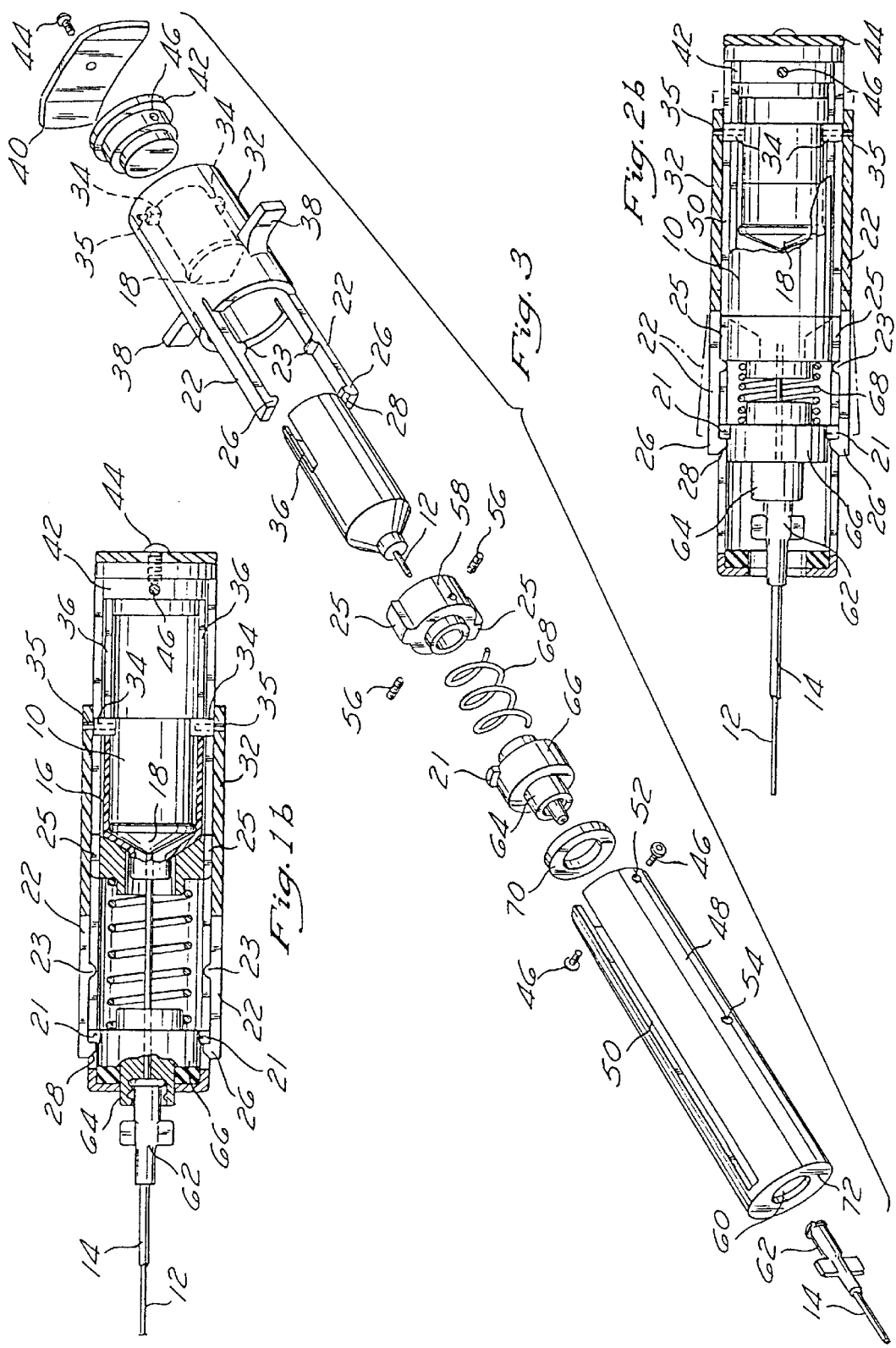

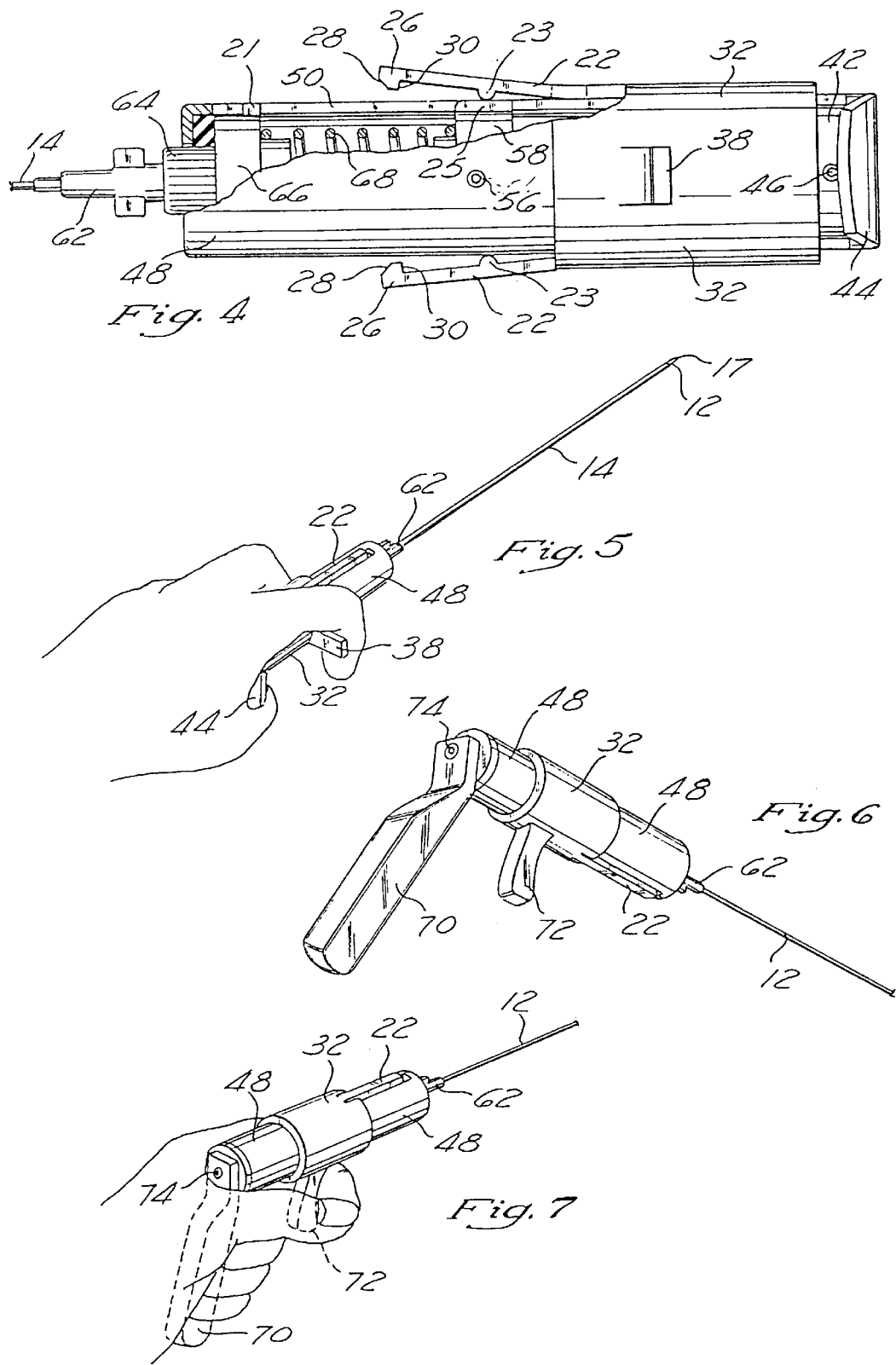

NEEDLE CORE BIOPSY DEVICE

RELATED APPLICATIONS

This patent application is a continuation-in-part patent application of U.S. Ser. No. 08/417,750, filed Apr. 6, 1995, now U.S. Pat. No. 5,560,373, which is a continuation-in-part patent application of U.S. Ser. No. 08/331,283, filed Oct. 27, 1994, now U.S. Pat. No. 5,469,860, which is a continuation-in-part patent application of U.S. Ser. No. 08/225,594, filed Apr. 11, 1994, now U.S. Pat. No. 5,511,556, all three of which are hereby incorporated by reference.

FIELD OF THE INVENTION

The present invention relates generally to tissue extraction devices, and more particularly to a hand-held needle biopsy device for extracting a tissue sample from a patent.

BACKGROUND OF THE INVENTION

Biopsy devices utilizing needle aspiration to extract tissue samples are well known to those skilled in the art. Such devices are extremely useful to obtain samples of tissue suspected of being cancerous, so that such tissue samples may be examined in order to confirm such suspected diagnosis. Such devices are frequently used when sampling suspected cancerous tissue in the lungs, liver, adrenal glands, kidneys, breasts, and prostate, as well as other body organs. Numerous other applications have also been found for these devices.

Generally, such biopsy devices extract a sample of tissue from a tissue mass by either drawing a tissue sample into a hollow needle via an external vacuum force or by severing and containing a tissue sample within a notch formed in a stylet. Typical of such devices utilizing a vacuum force are U.S. Pat. No. 5,246,011 issued to Cailouette and U.S. Pat. No. 5,183,052 issued to Terwilliger. Such devices contemplate advancing a hollow needle into a tissue mass and applying a vacuum force to draw a sample into the needle and hold the same therein while the tissue is extracted. Such devices, however, fail to adequately sever and contain such tissue samples because the vacuum force may not be sufficiently strong to sever and hold the sample within the biopsy needle.

Alternatively, other prior art biopsy devices utilize a biopsy needle with a tissue sample recovery notch formed thereon to extract a specimen, such as described in U.S. Pat. No. 3,477,423 issued to Griffith, often referred to as the TRU-CUT needle and U.S. Pat. No. 4,776,423 issued to Beraha et al. Such devices, however, suffer from the drawback of not effectively drawing a tissue sample of sufficient size into the biopsy notch on the cannula. Accordingly, such samples extracted by such biopsy needles may not provide sufficient tissue to perform an adequate examination and thus frequently require additional biopsies to be taken. Additionally, such needles suffer from the disadvantage of having to be advanced into the desired tissue site such that the needle may possibly extend beyond the tissue site, thus resulting in the recovery of an inaccurate or non-usable tissue sample or even resulting in injury to adjacent organs or structures due to such overpenetration.

Further attempts in the art have been made utilizing specially designed cannulas to enhance the cutting and recovery of tissue samples, as well as combining the application of a vacuum force to draw a tissue sample into a biopsy cavity prior to cutting the tissue contained therein. U.S. Pat. No. 4,708,147 issued to Haaga discloses a cannula for a biopsy needle designed to cut a sample of tissue and then applying a vacuum to the cannula such that the tissue is drawn into the cannula and thus retained therein for recovery. Additionally, U.S. Pat. No. 3,844,272 issued to Banko discloses a biopsy device wherein a suction force, created by a vacuum, draws a sample of tissue into a receiving compartment whereby two coaxial members are rotated relative to each other so that the members essentially coact to cut off the specimen and place it into a compartment. Such combination devices, however, fail to either sufficiently isolate a sample or fail to draw in a sample of sufficient size into a biopsy compartment. Additionally, such devices typically are difficult to maneuver and manipulate and are not necessarily accurate or effective enough to achieve their desired purpose.

Accordingly, there exists a substantial need in the art to provide a tissue sample extractor capable of effectively and efficiently drawing in a suitable sample of tissue and isolating the tissue sample within the biopsy device. Additionally, there is a need for a biopsy device that is easy to use and can effectively be manipulated by one hand in light of the fact that it is advantageous to perform such biopsy procedures wherein the physician user is allowed to have an additional free hand. Furthermore, there is need in the art to provide a tissue sample extractor that not only provides tissue samples of sufficient size, but allows the user to take multiple tissue samples without having to repeatedly puncture and penetrate the tissue mass. Further, it would be of even greater advantage to provide a tissue sample extractor having the above-mentioned features and also either utilizing a disposable cannula assembly, or being a completely disposable device.

SUMMARY OF THE INVENTION

The present invention specifically addresses and alleviates the above-mentioned deficiencies associated with the prior art. More particularly, the present invention comprises a needle biopsy device comprising a suction source, an inner cannula having a biopsy reservoir formed proximate a distal end thereof, and also having a lumen formed therein. The lumen provides fluid communication between the suction source and the biopsy reservoir. An outer cannula is slidably disposed about the inner cannula. The outer cannula has a cutter formed at the distal end thereof which is configured to cut sample tissue drawn into the biopsy reservoir by the suction source from the surrounding tissue.

According to the preferred embodiment of the present invention, the outer cannula has a distal position substantially covering the biopsy reservoir of the inner cannula and has a proximal position substantially exposing the biopsy reservoir of the inner cannula.

An actuating mechanism moves the outer cannula from the distal position to the proximal position thereof and facilitates the application of suction from the suction source to the biopsy reservoir. The actuator mechanism also moves the outer cannula from the proximal position thereof to the distal position thereof.

Moving the outer cannula from the distal position to the proximal position thereof and creating suction at the biopsy reservoir causes the tissue sample to be pulled into the biopsy reservoir. Moving the outer cannula from the proximal position to the distal position thereof causes the cutter to cut the tissue sample from surrounding tissue and capture the tissue sample within the biopsy reservoir.

The outer cannula is preferably configured so as to be removable from the inner cannula and the actuating mechanism, such that the inner cannula may be withdrawn from the outer cannula during a biopsy procedure, thereby leaving the outer cannula in place, within the patient. Thus, multiple tissue samples may be obtained without the need to re-insert the device for each tissue sample. That is, once a first tissue sample has been obtained, the outer cannula is merely disconnected from the actuating mechanism and the inner cannula, containing the tissue sample, is withdrawn from the outer cannula. The tissue sample is then removed from the inner cannula and the inner cannula is re-inserted into the outer cannula. This positions the inner cannula at a point proximate that where the first tissue sample was obtained. A plurality of additional tissue samples may be obtained by merely repeating this procedure, as desired. Thus, the trauma associated with repeatedly re-inserting the device is eliminated.

According to the preferred embodiment of the present invention, the biopsy reservoir comprises undercuts formed in the inner cannula at the distal and proximal ends of the biopsy reservoir. The undercuts form generally pointed members or fingers at either end of the biopsy reservoir. The proximal finger tends to prevent an excessive quantity of the tissue from being pulled into the lumen of the inner cannula by the suction applied thereto. The distal finger tends to prevent the inner cannula from moving relative to the lesion being sampled. The proximal finger can optionally be bent inwardly, so as to partially obscure the lumen of the inner cannula, and thereby more effectively retain tissue samples within the biopsy reservoir.

According to the preferred embodiment of the present invention, the suction source comprises a cylinder and a plunger cooperating so as to define a syringe. Thus, drawing the plunger from the syringe creates suction which is communicating through the lumen of the inner cannula to the biopsy reservoir thereof. The actuating mechanism draws the plunger so as to effect the creation of such suction within the biopsy reservoir.

The inner cannula comprises a closed distal end so as to facilitate easy insertion thereof and so as to maintain desirable suction within the biopsy reservoir. Preferably, the inner cannula comprises a pointed beveled distal end so as to further facilitate easy insertion thereof.

The distal end of the outer cannula, defining the cutter, is preferably formed to have a bevel. The bevel is preferably formed to define a point opposite (at 180° with respect to) the point at the tip of the inner cannula. The bevel formed upon the outer cannula is preferably ground to form a cutting edge. The bevel of the outer cannula is preferably oriented such that the point thereof moves across the opening of the biopsy reservoir so as to achieve effective cutting of the sample tissue from surrounding tissue. As those skilled in the art will appreciate, various different bevel angles and/or orientations are suitable.

According to the preferred embodiment of the present invention, the actuating mechanism comprises at least one gripper, preferably two opposed grippers for engaging detents formed upon or in mechanical communication with the outer cannula such that moving the gripper proximally also moves the detents proximally, thereby moving the outer cannula from the distal position thereof to the proximal position thereof.

The gripper further comprises first camming surface formed thereon. A second camming surface causes the grippers to disengage the detents when the first camming surface rides over the second camming surface. When the grippers disengage the detents, a biasing device, preferably a spring, urges the outer cannula rapidly back to the distal position thereof such that the tissue sample drawn via suction into a biopsy reservoir is quickly cut from surrounding tissue. Preferably, the detents which are engaged by the opposed grippers are formed upon a distal spring abutment formed to the outer cannula, which is abutted by the distal end of the spring, so as to urge the outer cannula distally.

The plunger and/or cylinder of the syringe are preferably configured such that vacuum is released when the plunger is approximately at the end of its outward stroke. Thus, suction at the biopsy reservoir stops so as to prevent the tissue sample from being undesirably drawn into the lumen of the inner cannula. This is preferably accomplished by configuring the plunger and/or cylinder such that air enters the cylinder once the plunger has been withdrawn sufficiently.

According to the preferred embodiment of the present invention, a slide is slidably disposed relative to the inner cannula. The grippers are formed to the slide in an opposed fashion such that the grippers are biased inwardly so as to grip the detents. The slide has a distal position wherein the grippers engage the detents and a proximal position wherein the grippers are caused to disengage the detents. Thus, the detents are engaged when the slide is in its distal position and remain engaged as the slide moves proximally until the slide approaches the proximal position thereof, wherein the grippers are caused to disengage the detents, thereby allowing the outer cannula to move distally at the urging of the spring.

Either a trigger or at least one, preferably two, finger holds are formed to the slide to facilitate pulling the slide proximally. Either a handle or a palm abutment is disposed generally stationary relative to the inner cannula, for facilitating proximal movement of the slide.

A resilient member or cushion slows the movement of the outer cannula as the outer cannula approaches the distal position thereof, and thus functions as a shock absorber to prevent damage to the needle biopsy device due to the impact caused by the spring rapidly moving the outer cannula distally.

Preferably, the vacuum source, inner cannula, outer cannula, and at least a portion of the actuating mechanism define a disposable assembly which is configured for removable attachment to a reusable handle. The trigger may, optionally, be formed so as to be reusable and be attached to the reusable handle. The reusable portion of the needle biopsy device of the present invention may, optionally, be formed so as to be autoclavable. Alternatively, the reusable portion may merely be sterilizable, as desired. The disposable portion of the present invention is sterilized and packaged by the manufacturer so as to remain in a sterilized condition until use.

These, as well as other advantages of the present invention, will be more apparent from the following description and drawings. It is understood that changes in the specific structure shown and described may be made within the scope of the claims without departing from the spirit of the invention.

Thus, according to the present invention, the inner cannula is positioned such that the biopsy reservoir formed therein is proximate the tissue to be sampled and the inner cannula does not move, e.g., does not translate, during the cutting process. Thus, in contrast to needle biopsy devices of the prior art, the location where such tissue samples are taken is easily controllable.

BRIEF DESCRIPTION OF THE DRAWINGS

FIG. 1 is a perspective view of a first embodiment of the needle biopsy device of the present invention showing the slide and the outer cannula disposed in the distal positions thereof, wherein the grippers have engaged the detents so as to facilitate moving the outer cannula from the distal position thereof to the proximal position thereof, while simultaneously compressing the spring;

FIG. 1a is an enlarged perspective view of the distal portion of the inner and outer cannulas of FIG. 1, showing the outer cannula in the distal position thereof, so as to cover the biopsy reservoir formed in the inner cannula;

FIG. 1b is a cross-sectional side view of the needle biopsy device of FIG. 1, showing the slide in the distal position thereof;

FIG. 2 is a perspective view of the needle biopsy device of FIG. 1 showing the slide and the outer cannula in the proximal positions thereof, wherein the grippers are about to release the detents so as to cause the compressed spring to move the outer cannula rapidly back to the distal position thereof, thereby cutting a tissue sample and capturing that tissue sample within the biopsy reservoir;

FIG. 2a is an enlarged perspective view of the distal portion of the inner and outer cannulas, showing the outer cannula in the proximal position thereof, so as to expose the biopsy reservoir formed in the inner cannula;

FIG. 2b is a cross-sectional side view of the needle biopsy device of FIG. 2, showing the slide in the proximal position thereof, wherein the grippers are about to release the detents so as to allow the compressed spring to move the outer cannula back to the distal position thereof;

FIG. 2c is an enlarged perspective view of the distal portion of the inner and outer cannulas, showing the undercut distal and proximal ends of the biopsy reservoir formed in the inner cannula;

FIG. 3 is an exploded perspective view of the needle biopsy device of FIG. 1, showing the actuating mechanism and the suction source;

FIG. 4 is an enlarged side view, partially in cross section, showing the needle biopsy device of FIG. 1 with the slide in the proximal position thereof, after the grippers have disengaged the detents and the spring has moved the outer cannula back to the distal position thereof;

FIG. 5 shows a user holding the first embodiment of the needle biopsy device of the present invention as it is to be used in a needle biopsy procedure;

FIG. 6 is a perspective view of a second embodiment of the needle biopsy device of the present invention, wherein a handle and trigger are used instead of a palm abutment and two finger holds; and FIG. 7 shows a user holding the second embodiment of the needle biopsy device of the present invention as it is to be used in a needle biopsy procedure.

DETAILED DESCRIPTION OF THE PREFERRED EMBODIMENT

The detailed description set forth below in connection with the appended drawings is intended as a description of the presently preferred embodiments of the present invention, and is not intended to represent the only forms in which the present invention may be constructed or utilized. The description sets forth the functions and sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The needle biopsy device of the present invention is illustrated in FIGS. 1–7 which depict two presently preferred embodiments of the invention. The first embodiment of the invention is depicted in FIGS. 1–5 and the second embodiment of the present invention is depicted in FIGS. 6 and 7. Referring now to FIGS. 1–4, the needle biopsy device of the present invention generally comprises a suction source 10, (best shown in FIGS. 1b, 2b, and 3), preferably comprised of a cylinder 16 and a plunger 18 defining a syringe. An inner cannula 12 has a biopsy reservoir 13 (as best shown in FIGS. 2a and 2c) formed proximate the distal end 17 thereof. The inner cannula 12 also has a lumen 15 formed therethrough, so as to provide fluid communication between the suction source 10 and the biopsy reservoir 13.

An outer cannula 14 is slidably disposed about the inner cannula 12, such that the inner cannula 12 is disposed within the lumen of the outer cannula 14. The outer cannula 14 has a cutter 20 formed at the distal end thereof. The cutter 20 is preferably formed as a bevel formed at the distal end of the outer cannula 14. The bevel is preferably configured such that the point defined thereby travels across the opening of the biopsy reservoir 13 to effect cutting. The bevel is preferably oriented such that the point thereof travels across the opening defined by the biopsy reservoir 13, so as to effectively cut the tissue sample from surrounding tissue. Those skilled in the art will appreciate that various different angles and orientations of bevels are likewise suitable.

The desired rotational orientation of the cutting outer cannula 14 with respect to the biopsy reservoir 13 may be maintained by means of a single lead screw which facilitates attachment of the outer cannula 14 via Luer lock fitting 62 to Luer fitting 64, or by means of a channel lock, indexed double lead screw (the index assuring correct mounting orientation), bayonet mount, or spline as an alternative. The spline is formed to one of the outer cannula and the cannula mount and is received within a channel formed in the other one thereof. Those skilled in the art will appreciate various different flanges, detents, tracks, slots, channels, etc. may be utilized to maintain desired orientation of the cutting bevel 20 of the outer cannula 14 with respect to the biopsy reservoir 13.

The outer cannula 14 has a distal position, as shown in FIGS. 1, 1a, and 1b and also has a proximal position as shown in FIGS. 2, 2a, and 2b. When in the distal position thereof, the outer cannula 14 covers the biopsy reservoir 13 formed in the inner cannula 12 and when in the proximal position thereof, the outer cannula 14 exposes the biopsy reservoir 13.

An actuating mechanism for moving the outer cannula 14 from the distal position to the proximal position thereof, for facilitating the application of suction to the biopsy reservoir 13, and for rapidly moving the outer cannula 14 from the proximal position to the distal position thereof so as to effect cutting, comprises a pair of grippers 22 which engage a complementary pair of detents 21. The detents 21 are in mechanical communication with the outer cannula 14 such that moving the detents causes the outer cannula 14 to move likewise. The detents 21 are preferably formed upon the distal spring abutment 66. The grippers 22 preferably comprise engaging pawls 26 formed at the distal ends thereof. Each engaging pawl 26 preferably comprises a camming surface 28 for riding up over the detents 21 and a catch surface 30 (as best shown in FIG. 4) for engaging the detents 21. Grippers 22 further comprise cams 23, preferably formed upon the inner surface thereof proximal the engaging pawls 26, so as to effect disengagement of the engaging pawls 26 from the detents 21 when the cams 23 ride upon a camming surface 25, preferably formed upon the proximal spring abutment 58.

According to the preferred embodiment of the present invention, the actuating mechanism further comprises a slide 32 to which the grippers 22 are attached.

Preferably, the slide 32 slides along a generally cylindrical body 48. The cylinder 16 is disposed within the body 48 and remains stationery with respect thereto, as the slide 32 is moved proximally. The inner cannula 12 is attached to the cylinder 16, such that suction produced within the cylinder 16 is transmitted through the lumen 15 of the inner cannula 12 to the biopsy reservoir 13 thereof. The cylinder 16, and thus the inner cannula 12, are rigidly mounted within the body 48.

Standoffs 34 (best shown in FIGS. 1b, 2b, and 3) attach the plunger 18 to the slide 32. The standoffs 34 function as followers and slide within slots or grooves 36 formed upon two diametrically opposed sides of the cylinder 16 or may be guided by slots 50, so as to prevent undesirable rotation of the slide 32 relative thereto. Thus, the desired orientation of the grippers 22 relative to the detents 21 is maintained. The standoffs 34 may be attached to the slide 32 via metal pins 35. Optionally, the standoffs 34 may be integrally molded with the slide 32, or attached via a snap fit or other means.

The grooves or slots 36 are of sufficient length to allow the front of the plunger 18 to clear the cylinder 16 at the rearmost position of the stroke, and thus allow air to enter the cylinder 16. This will allow loss of suction after the cutting cannula 14 has returned to the distal position thereof. Thus, according to the preferred embodiment of the present invention, vacuum is released just after a biopsy sample is cut. Alternatively, other grooves or slots may be placed anywhere on the periphery of cylinder 16 to allow vacuum release at the desired moment. Thus, by breaking the vacuum at the end of the plunger's 18 stroke, the spring force caused by vacuum within the cylinder 16 is eliminated, and the sample is prevented from being undesirably drawn into the lumen of the inner cannula 12.

Spring 68 is disposed intermediate proximal 58 and distal 66 spring abutments, so as to urge distal spring abutment 66, to which the outer cannula 14 is attached, distally. Proximal spring abutment 58 is maintained stationary relative to the body 48 via set screw 56. The camming surfaces 25 are formed upon the outer most periphery of the proximal spring abutment 58. An alternate embodiment combines the functions of the proximal spring abutment 58 and camming surfaces 25 into the cylinder 16, by forming the camming surfaces 25 and abutment 55 as integral portions of the cylinder 16. Resilient washer 70 is disposed intermediate distal spring abutment 66 and the distal end 72 of body 48 and is preferably adhesively bonded in place, so as to absorb the impact of the distal spring abutment 66 as the distal spring abutment 66 is driven distally at the urging of spring 68, during operation of the needle biopsy device of the present invention.

According to the preferred embodiment of the present invention, finger holds 38 are formed in diametrically opposed positions upon the slide 32, so as to facilitate proximal movement of the slide 32. Further, palm abutment 40 is attached to end cap 42 via screw 44 and end cap 42 is attached to the distal end of body 48 via screws 46. Body 48 comprises slots 50 within which grippers 22, particularly the engaging pawls 26 and cams 23 thereof, travel. Body 48 further comprises apertures 52 for receiving screws 46 which attach the end cap 42 thereto and apertures 54 for receiving set screws 56 which attach proximal spring abutment 58 thereto. Alternatively, the body 48, end cap 42, and palm abutment 40 are formed as a single, integral unit.

Body 48 further comprises frontal opening 60 for receiving the proximal end of the outer cannula 14, preferably having a Luer lock fitting 62 formed thereon which attaches to Luer fitting 64 of the distal spring abutment 66. The outer cannula 14 is preferably removably attachable to the needle biopsy device of the present invention, preferably to the distal spring abutment 66 thereof. Such removable attachment of the outer cannula 14 facilitates the taking of multiple biopsy tissue samples without requiring repeated introduction of the device, as discussed in detail below.

With particular reference to FIG. 2c, the biopsy reservoir 13 preferably comprises an undercut 82 formed at the distal end thereof and a similar undercut 83 formed at the proximal end thereof. The undercut 82 formed at the distal end of the biopsy reservoir 13 defines a generally pointed member or first finger 80 and, similarly, the undercut 83 formed at the proximal end of the biopsy reservoir 13 defines a generally pointed member or second finger 81.

As discussed above, the first finger 80 formed at the distal end of the biopsy reservoir 13 tends to prevent undesirable proximal movement of the needle cannula during the cutting process, particularly undesirable pulling of the needle or inner cannula 12 out of the lesion to be sampled. The first finger 80 acts as a hook to secure the inner cannula 12 to the tissue being sampled. The second finger 81 tends to prevent an excessive quantity of the tissue sample from being drawn into the lumen of the first cannula 12 as suction is applied thereto. In both instances, such undesirable movement of the needle cannula and tissue sample is substantially prevented as the generally pointed fingers 80, 81 dig into and hold the tissue sample in a desirable manner.

The fingers 81 are optionally bent inwardly, so as to partially obscure the lumen of the inner cannula, and thereby more effectively retain a tissue sample within the biopsy reservoir.

Optionally, a generally tubular vanity shield 90 (FIG. 2) is configured so as to substantially cover the actuating mechanism, so as to enhance the aesthetic appeal of the device. The vanity shield 90 preferably comprises a mounting partition 92 formed therein to facilitate attachment of the vanity shield 90 to the needle biopsy device. A circular opening 94 formed in the mounting partition 92 is sized to snugly receive the Luer fitting 64, preferably providing a sufficiently tight fit thereto so as to maintain the vanity shield 90 in attachment with the needle biopsy device. Thus, the vanity shield 90 substantially hides the working components of the needle biopsy device from view. Those skilled in the art will appreciate that various other configurations of the vanity shield 90 and means for attaching the vanity shield 90 to the needle biopsy device are likewise suitable.

Having thus described the structure of the first embodiment of the present invention in detail, it may be beneficial to describe the operation thereof. With particular reference to FIGS. 1, 1a, and 1b, the slide 32 is positioned distally such that the grippers 22 thereof engage the detents 21 of the distal spring abutment 66. With the slide in this distal position, the outer cannula 14 covers the biopsy reservoir 13 formed in the inner cannula 12. The inner 12 and outer 14 cannulas are inserted into the patient such that the biopsy reservoir 13 is disposed within or proximate the tissue to be sampled.

With particular reference to FIG. 5, the slide is then drawn proximally so as to compress spring 68 and simultaneously create the suction via the syringe defined by cylinder 16 and plunger 18. The suction is transmitted via the lumen 15 of the inner cannula 12 to the biopsy reservoir 13.

As the slide 32 is drawn proximally, the outer cannula 14 is likewise moved proximally such that the biopsy reservoir 13 is exposed. The suction communicated to the biopsy reservoir 13 draws tissue thereinto.

With particular reference to FIGS. 2, 2a, and 2b, when the slide 32 nears the proximal position thereof, cams 23 formed upon the grippers 22 contact camming surfaces 25 formed upon the proximal spring abutment 58 such that the grippers 22 are urged outwardly and thereby caused to disengage the detents 21 of the distal spring abutment 66. As those skilled in the art will appreciate, any desired number of cams 23 and grippers 22 may be utilized to engage a complimentary number of detents so as to effect withdrawal of the outer cannula 14. Thus, single, double (as illustrated), triple, etc., grippers 22 may be utilized. Disengagement of the grippers 22 from the detents 21 of the distal spring abutment 66 allows the spring 68 to urge the distal spring abutment 66 rapidly distally, thus driving the outer cannula 14 back to the distal position thereof, wherein the biopsy reservoir 13 is covered thereby. In being driven distally, the cutter 20 formed upon the distal end of the outer cannula 14 cuts that tissue drawn into the biopsy reservoir 13 from surrounding tissue so as to capture the sampled tissue within the biopsy reservoir 13. After cams 23 contact camming surfaces 25, thereby releasing the proximal spring abutment 58, additional rearward movement of slide 32 causes plunger 18 to move into a position such as to release vacuum by allowing air to enter the cylinder 16 via grooves 36. Such vacuum release preserves the integrity of the cut sample.

The resilient washer 70 cushions the impact of the distal spring abutment 66 as it is driven toward to the distal end 72 of the body 48.

The inner 12 and outer 14 cannulas are withdrawn from the patient and the slide 32 is withdrawn sufficiently to cause the biopsy reservoir 13 to be uncovered by the outer cannula 14 or the outer cannula 14 may be removed from inner cannula 12 such that the tissue sample may easily be removed therefrom.

The plunger 18 and the slide 32 may be returned to the distal positions thereof after use of the present invention via either manual operation or by utilizing an optional spring return (not shown).

When it is desired to collect a plurality of biopsy tissue samples, this may be accomplished with minimal trauma to the patient by disconnecting the outer cannula 14, preferably via the Luer lock thereof, from the needle biopsy device of the present invention and withdrawing the inner cannula 12, as well as the biopsy tissue sample contained within the biopsy reservoir 13 thereof through the lumen of the outer cannula 14. The biopsy sample is then removed from the biopsy reservoir 13 and the inner cannula 12 is re-inserted into the outer cannula 14 and the outer cannula 14 is reconnected to the needle biopsy device. The needle biopsy device of the present invention may then be utilized to collect further biopsy tissue samples in the manner described above. This process may be repeated until sufficient biopsy tissue samples have been collected.

Referring now to FIGS. 6 and 7, a second embodiment of the needle core biopsy device of the present invention is shown. In the second embodiment of the present invention, the palm abutment 40 is replaced with a handle 70 and the finger grips 38 are replaced with a trigger 72, such that the needle core biopsy device may be held and operated in the traditional manner of a gun as illustrated in FIG. 7. The user merely grasps the handle 70 of the device within the palm of the user's hand and then uses the index and/or middle finger to withdraw the slide 32. Operation of the second embodiment of the present invention is otherwise identical to the operation of the first embodiment thereof.

Thus, according to the present invention, the handle may comprise either a pistol grip type of handle 17 as shown in FIGS. 6 and 7 or a palm abutment type of handle 44 as shown in FIGS. 4 and 5, as desired.

All or selected portions of the needle core biopsy device of the present invention may be fabricated so as to be disposable. Alternatively, the needle core biopsy device of the present invention may be formed so as to be reusable. Further, any reusable portions of the needle core biopsy device are formed so as to be either sterilizable or autoclavable.

According to the preferred embodiment of the present invention, the handle 70 is formed so as to be reusable. Optionally, the trigger 72, which may be formed as part of the handle so as to slide relative thereto, is formed so as to be reusable. Thus, the remainder of the present invention is thus formed so as to be disposable. Thus, the disposable portion of the present invention snaps or fits into the reusable handle/trigger assembly, so as to facilitate convenient and easy use thereof.

The present invention further facilitates the taking of multiple sequential tissue samples from a common location. This may be accomplished by disconnecting the Luer lock 62 of the outer cannula 14 from the Luer lock 64 of the body 48 and leaving the outer cannula 14 in place within the patient while the inner cannula 12 is removed from the outer cannula 14 and the tissue sample is removed from the biopsy reservoir 13. The inner cannula 12 may then be reinserted into the outer cannula 14 and the Luer lock 62 of the outer cannula 14 reattached to the Luer lock 64 of the body 48 and the process repeated, as desired.

It is understood that the exemplary needle core biopsy device described herein and shown in the drawings represents only presently preferred embodiments of the invention. Indeed, various modifications and additions may be made to such embodiments without departing from the spirit and scope of the invention. For example, as those skilled in the art will appreciate, the body 22 and slide 32 of the present invention need not be cylindrical in configuration, as shown and described, but rather may alternatively be of any convenient shape, e.g., triangular, square, rectangular, hexagonal, octagonal, elliptical, etc. Furthermore, those skilled in the art will appreciate that various different vacuum sources are suitable for use in the present invention. For example, rather than the syringe illustrated and discussed, an in-house or external vacuum source may be utilized with either a built-in vacuum application valve which applies vacuum as the slide is withdrawn or an external vacuum application valve, such as one operated by a foot pedal. As such, these and other modifications and additions may be obvious to those skilled in the art may be implemented to adapt the present invention for use in a variety of different applications.

Thus, according to the present invention, the inner cannula 12 is positioned such that the biopsy reservoir 13 formed therein is proximate the tissue to be sampled and the inner cannula the inner cannula 12 does not move, e.g., does not translate, during the cutting process. Thus, in contrast to needle biopsy devices of the prior art, the location where such tissue samples are taken is easily controllable.

What is claimed is:

1. A needle biopsy device comprising:
   a) a suction source;
   b) an inner cannula having a biopsy reservoir formed proximal a distal end thereof, and also having a lumen formed therein, said lumen providing fluid communication between the suction source and the biopsy reservoir;
   c) an outer cannula slidably disposed about said inner cannula, said outer cannula having a cutter formed at a distal end thereof, said outer cannula having a distal position substantially covering the biopsy reservoir of said inner cannula and having a proximal position substantially exposing the biopsy reservoir of said inner cannula;
   d) an actuating mechanism for moving said outer cannula from the distal position to the proximal position thereof, for facilitating the application of suction from said suction source to the biopsy reservoir, and for moving said outer cannula from the proximal position to the distal position thereof, wherein said suction source comprises a cylinder and a plunger cooperating to define a syringe and said actuating mechanism moves the plunger within the cylinder so as to apply suction to the biopsy reservoir, and wherein the actuator mechanism comprises:
      1) at least one detent formed to said outer cannula such that moving said detent(s) proximally causes said outer cannula to move from the distal position thereof to the proximal position thereof;
      2) at least one gripper, the number of grippers corresponding generally to the number of detents, for engaging said detent(s) and for moving said detent(s) proximally, said gripper(s) having a first camming surface formed thereon;
      3) at least one second camming surface, the number of second camming surfaces corresponding generally to the number of first camming surfaces, for causing said gripper(s) to disengage said detent(s) when said outer cannula is proximate the proximal position thereof; and
      4) a biasing device for urging said outer cannula to the distal position thereof after said gripper(s) disengage said detent(s); and
   e) wherein moving said outer cannula from the distal position to the proximal position thereof and creating suction at the biopsy reservoir causes a tissue sample to be pulled into the biopsy reservoir and wherein moving said outer cannula from the proximal position to the distal position thereof causes the cutter to cut the tissue sample from surrounding tissue and also captures the tissue sample within the biopsy reservoir.

2. The needle biopsy device as recited in claim 1, further comprising:
   a) a slide slidably disposed relative to said inner cannula, said gripper(s) being formed to said slide, said slide having a distal position wherein said gripper(s) engage said detent(s) and having a proximal position wherein said gripper(s) disengage said detent(s); and
   b) one of a trigger and at least one finger hold formed to said slide, for pulling said slide approximately; and
   c) one of a handle and a palm abutment disposed generally stationery relative to said inner cannula, for facilitating proximal movement o said slide.

3. The needle biopsy device as recited in claim 1, wherein said biasing device comprises a spring.

4. A needle biopsy device comprising:
   a) a cylinder and a plunger cooperating to define a syringe;
   b) an inner cannula having a biopsy reservoir formed proximate a distal end thereof, and also having a lumen, said lumen providing fluid communication between the syringe and the biopsy reservoir;
   c) an outer cannula slidably disposed about said inner cannula, said outer cannula having a cutter formed at a distal end thereof, said outer cannula having a distal position substantially covering the biopsy reservoir of said inner cannula and having a proximal position substantially exposing the biopsy reservoir of said inner cannula;
   d) an actuating mechanism for moving said outer cannula from the distal position to the proximal position thereof, for facilitating the application of suction from said syringe to the biopsy reservoir, and for moving said outer cannula from the proximal position to the distal position thereof, said actuating mechanism comprising:
      i) at least one detent in communication with said outer cannula such that moving said detent(s) proximally causes said outer cannula to move from the distal position thereof to the proximal position thereof,
      ii) at least one gripper, the number of grippers corresponding generally to the number of detents, for engaging said detent(s) and for moving said detent(s) proximally, said gripper(s) having a first camming surface formed thereon;
      iii) at least one second camming surface, the number of second camming surfaces corresponding to the number of first camming surfaces, generally for causing said gripper(s) to disengage said detent(s) when said outer cannula is at the second position thereof; and
      v) a spring for urging said outer cannula to the first position thereof after said gripper(s) disengage said detent(s); and
   e) wherein said syringe, inner cannula, said outer cannula, and at least a portion of said actuating mechanism define a disposable assembly, said disposable assembly configured for removable attachment to a reusable handle.

5. The needle biopsy device as recited in claim 4, further comprising a slide slidably disposed relative to said inner cannula, said gripper(s) being formed to said slide, said slide having a distal position wherein said gripper(s) engage said detent(s) and having a proximal position wherein said gripper(s) disengage said detent(s).

6. The needle biopsy device as recited in claim 4, further comprising a trigger for pulling said slide proximally.

7. The needle biopsy device as recited in claim 4, further comprising a handle disposed generally stationary relative to said inner cannula, for facilitating proximal movement of said slide.

8. The needle biopsy device as recited in claim 4, further comprising a resilient member for slowing the movement of said outer cannula as said outer cannula approaches the distal position thereof.

9. A needle biopsy device comprising:
   a) a cylinder and a plunger cooperating to define a syringe;
   b) an inner cannula having a biopsy reservoir formed proximate a distal end thereof, and also having a lumen, said lumen providing fluid communication between the syringe and the biopsy reservoir, said inner cannula having a closed distal end;

c) an outer cannula slidably disposed about said inner cannula, said outer cannula having a cutter formed at a distal end thereof, said outer cannula having a distal position substantially covering the biopsy reservoir of said inner cannula and having a proximal position substantially exposing the biopsy reservoir of said inner cannula;

d) an actuating mechanism for moving said outer cannula from the distal position to the proximal position thereof, for facilitating the application of suction from said syringe to the biopsy reservoir, and for moving said outer cannula from the proximal position to the distal position thereof, said actuating mechanism comprising:

e) wherein said cylinder and plunger are configured such that air enters the cylinder after the outer cannula moves from the proximal to the distal position thereof, such that suction to the biopsy reservoir is terminated.

10. A needle biopsy device comprising:

a) a cylinder and a plunger cooperating to define a syringe;

b) an inner cannula having a biopsy reservoir formed proximate a distal end thereof, and also having a lumen, said lumen providing fluid communication between the syringe and the biopsy reservoir, said inner cannula having a closed distal end;

c) an outer cannula slidably disposed about said inner cannula, said outer cannula having a cutter formed at a distal end thereof, said outer cannula having a distal position substantially covering the biopsy reservoir of said inner cannula and having a proximal position substantially exposing the biopsy reservoir of said inner cannula;

d) an actuating mechanism for moving said outer cannula from the distal position to the proximal position thereof, for facilitating the application of suction from said syringe to the biopsy reservoir, and for moving said outer cannula from the proximal position to the distal position thereof, said actuating mechanism comprising:

i) at least one detent formed to said outer cannula such that moving said detent(s) proximally causes said outer cannula to move from the first position thereof to the second position thereof;

ii) at least one gripper, the number of grippers corresponding generally to the number of detents, for engaging said detent(s) and for moving said detent(s) proximally, said gripper(s) having a first camming surface formed thereon;

iii) at least one second camming surface, the number of second camming surfaces corresponding to the number of first camming surfaces, generally for causing said gripper(s) to disengage said detent(s) when said outer cannula is at the second position thereof;

iv) a spring for urging said outer cannula to the first position thereof after said gripper(s) disengage said detent(s);

e) a slide slidably disposed relative to said inner cannula, said gripper(s) being formed to said slide, said slide having a distal position wherein said gripper(s) engage said detent(s) and having a proximal position wherein said gripper(s) disengage said detent(s), said slide being attached to said piston such that said piston generally moves along therewith;

f) a trigger for pulling said slide proximally;

g) a handle disposed generally stationery relative to said inner cannula, for facilitating proximal movement of said slide; and h) wherein the piston and slide are configured to be returned to the distal positions thereof by one of manual operation and a spring return, after actuation of said actuating mechanism.

11. A needle biopsy device comprising:

a) a cylinder and a plunger cooperating to define a syringe;

b) an inner cannula having a biopsy reservoir formed proximate a distal end thereof, and also having a lumen, said lumen providing fluid communication between the syringe and the biopsy reservoir, said inner cannula having a closed distal end;

c) an outer cannula slidably disposed about said inner cannula, said outer cannula having a cutter formed at a distal end thereof, said outer cannula having a distal position substantially covering the biopsy reservoir of said inner cannula and having a proximal position substantially exposing the biopsy reservoir of said inner cannula;

d) an actuating mechanism for moving said outer cannula from the distal position to the proximal position thereof, for facilitating the application of suction from said syringe to the biopsy reservoir, and for moving said outer cannula from the proximal position to the distal position thereof, said actuating mechanism comprising:

i) at least one detent formed to said outer cannula such that moving said detent(s) proximally causes said outer cannula to move from the first position thereof to the second position thereof;

ii) at least one gripper, the number of grippers corresponding generally to the number of detents, for engaging said detent(s) and for moving said detent(s) proximally, said gripper(s) having a first camming surface formed thereon;

iii) at least one second camming surface, the number of second camming surfaces corresponding to the number of first camming surfaces, generally for causing said gripper(s) to disengage said detent(s) when said outer cannula is at the second position thereof;

iv) a spring for urging said outer cannula to the first position thereof after said gripper(s) disengage said detent(s);

e) a slide slidably disposed relative to said inner cannula, said gripper(s) being formed to said slide, said slide having a distal position wherein said gripper(s) engage said detent(s) and having a proximal position wherein said gripper(s) disengage said detent(s);

f) a trigger for pulling said slide proximally; and g) a handle disposed generally stationery relative to said inner cannula, for facilitating proximal movement of said slide, wherein said handle comprises one of:
(i) a pistol grip; and
(ii) a palm abutment.

12. A needle biopsy device comprising:

a) a cylinder and a plunger cooperating to define a syringe;

b) an inner cannula having a biopsy reservoir formed proximate a distal end thereof, and also having a lumen, said lumen providing fluid communication between the syringe and the biopsy reservoir, said inner cannula having a closed distal end;

c) an outer cannula slidably disposed about said inner cannula, said outer cannula having a cutter formed at a distal end thereof, said outer cannula having a distal position substantially covering the biopsy reservoir of said inner cannula and having a proximal position substantially exposing the biopsy reservoir of said inner cannula;
d) an actuating mechanism for moving said outer cannula from the distal position to the proximal position thereof, for facilitating the application of suction from said syringe to the biopsy reservoir, and for moving said outer cannula from the proximal position to the distal position thereof, said actuating mechanism comprising:
 i) at least one detent formed to said outer cannula such that moving said detent(s) proximally causes said outer cannula to move from the first position thereof to the second position thereof;
 ii) at least one gripper, the number of grippers corresponding generally to the number of detents, for engaging said detent(s) and for moving said detent(s) proximally, said gripper(s) having a first camming surface formed thereon;
 iii) at least one second camming surface, the number of second camming surfaces corresponding to the number of first camming surfaces, generally for causing said gripper(s) to disengage said detent(s) when said outer cannula is at the second position thereof;
 iv) a spring for urging said outer cannula to the first position thereof after said gripper(s) disengage said detent(s);
e) a slide slidably disposed relative to said inner cannula, said gripper(s) being formed to said slide, said slide having a distal position wherein said gripper(s) engage said detent(s) and having a proximal position wherein said gripper(s) disengage said detent(s);
f) a trigger for pulling said slide proximally;
g) a handle disposed generally stationery relative to said inner cannula, for facilitating proximal movement of said slide; and
h) wherein rotational orientation of said outer cannula relative to said biopsy reservoir is maintained via one of:
 (i) a single lead screw;
 (ii) an indexed double lead screw;
 (iii) a spline; and
 (iv) a bayonet mount.

13. A needle biopsy device comprising:
a) a suction source;
b) an inner cannula having a biopsy reservoir formed proximal a distal end thereof, and also having a lumen formed therein, said lumen providing fluid communication between the suction source and the biopsy reservoir;
c) an outer cannula slidably disposed about said inner cannula, said outer cannula having a cutter formed at a distal end thereof, said outer cannula having a distal position substantially covering the biopsy reservoir of said inner cannula and having a proximal position substantially exposing the biopsy reservoir of said inner cannula;
d) an actuating mechanism for moving said outer cannula from the distal position to the proximal position thereof, for facilitating the application of suction from said suction source to the biopsy reservoir, and for moving said outer cannula from the proximal position to the distal position thereof;
e) a resilient member for slowing the movement of said outer cannula as said outer cannula approaches the distal position thereof; and
f) wherein moving said outer cannula from the distal position to the proximal position thereof and creating suction at the biopsy reservoir causes a tissue sample to be pulled into the biopsy reservoir and wherein moving said outer cannula from the proximal position to the distal position thereof causes the cutter to cut the tissue sample from surrounding tissue and also captures the tissue sample within the biopsy reservoir.

14. A needle biopsy device comprising:
a) a suction source;
b) an inner cannula having a biopsy reservoir formed proximal a distal end thereof, and also having a lumen formed therein, said lumen providing fluid communication between the suction source and the biopsy reservoir;
c) an outer cannula slidably disposed about said inner cannula, said outer cannula having a cutter formed at a distal end thereof, said outer cannula having a distal position substantially covering the biopsy reservoir of said inner cannula and having a proximal position substantially exposing the biopsy reservoir of said inner cannula;
d) an actuating mechanism for moving said outer cannula from the distal position to the proximal position thereof, for facilitating the application of suction from said suction source to the biopsy reservoir, and for moving said outer cannula from the proximal position to the distal position thereof; and
e) wherein moving said outer cannula from the distal position to the proximal position thereof and creating suction at the biopsy reservoir causes a tissue sample to be pulled into the biopsy reservoir and wherein moving said outer cannula from the proximal position to the distal position thereof causes the cutter to cut the tissue sample from surrounding tissue and also captures the tissue sample within the biopsy reservoir, and further wherein said vacuum source, said inner cannula, said outer cannula, and at least a portion of said actuating mechanism define a disposable assembly, said disposable assembly configured for removable attachment to the reusable handle.

15. The needle biopsy cannula as recited in claim 14, further comprising a trigger movably attached to said reusable handle.

16. The needle biopsy device as recited in claim 14, wherein said handle is autoclavable.

17. A needle biopsy device comprising:
a) a suction source;
b) an inner cannula having a biopsy reservoir formed proximal a distal end thereof, and also having a lumen formed therein, said lumen providing fluid communication between the suction source and the biopsy reservoir;
c) an outer cannula slidably disposed about said inner cannula, said outer cannula having a cutter formed at a distal end thereof, said outer cannula having a distal position substantially covering the biopsy reservoir of said inner cannula and having a proximal position substantially exposing the biopsy reservoir of said inner cannula;
d) an actuating mechanism for moving said outer cannula from the distal position to the proximal position thereof, for facilitating the application of suction from said suction source to the biopsy reservoir, and for moving said outer cannula from the proximal position to the distal position thereof;
e) wherein said suction source comprises a cylinder and a plunger cooperating to define a syringe and said actuating mechanism moves the plunger within the cylinder so as to apply suction to the biopsy reservoir, and wherein one of said cylinder and said plunger comprises at least one slot and the other of said cylinder and said plunger comprises at least one follower, said follower(s) moving within said slot(s) to maintain orientation of the plunger relative to the cylinder; and f) wherein moving said outer cannula from the distal position to the proximal position thereof and creating suction at the biopsy reservoir causes a tissue sample to be pulled into the biopsy reservoir and wherein moving said outer cannula from the proximal position to the distal position thereof causes the cutter to cut the tissue sample from surrounding tissue and also captures the tissue sample within the biopsy reservoir.

18. A needle biopsy device comprising:

a) a suction source;

b) an inner cannula having a biopsy reservoir formed proximal a distal end thereof, and also having a lumen formed therein, said lumen providing fluid communication between the suction source and the biopsy reservoir;

c) an outer cannula slidably disposed about said inner cannula, said outer cannula having a cutter formed at a distal end thereof, said outer cannula having a distal position substantially covering the biopsy reservoir of said inner cannula and having a proximal position substantially exposing the biopsy reservoir of said inner cannula;

d) an actuating mechanism for moving said outer cannula from the distal position to the proximal position thereof, for facilitating the application of suction from said suction source to the biopsy reservoir, and for moving said outer cannula from the proximal position to the distal position thereof;

e) wherein said suction source comprises a cylinder and a plunger cooperating to define a syringe and said actuating mechanism moves the plunger within the cylinder so as to apply suction to the biopsy reservoir, and wherein said cylinder comprises a plurality of slots and said plunger comprises a corresponding plurality of followers, said followers moving within said slots to maintain orientation of the plunger relative to the cylinder; and f) wherein moving said outer cannula from the distal position to the proximal position thereof and creating suction at the biopsy reservoir causes a tissue sample to be pulled into the biopsy reservoir and wherein moving said outer cannula from the proximal position to the distal position thereof causes the cutter to cut the tissue sample from surrounding tissue and also captures the tissue sample within the biopsy reservoir.

19. A needle biopsy device comprising:

a) a suction source;

b) an inner cannula having a biopsy reservoir formed proximal a distal end thereof, and also having a lumen formed therein, said lumen providing fluid communication between the suction source and the biopsy reservoir;

c) an outer cannula slidably disposed about said inner cannula, said outer cannula having a cutter formed at a distal end thereof, said outer cannula having a distal position substantially covering the biopsy reservoir of said inner cannula and having a proximal position substantially exposing the biopsy reservoir of said inner cannula;

d) an actuating mechanism for moving said outer cannula from the distal position to the proximal position thereof, for facilitating the application of suction from said suction source to the biopsy reservoir, and for moving said outer cannula from the proximal position to the distal position thereof;

e) at least one of:

1) an undercut formed in said inner cannula at a distal end of said biopsy reservoir so as to define a first finger, said first finger configured so as to inhibit movement of the tissue sample distally into the lumen of said inner cannula as the outer cannula moves from the proximal position to the distal position thereof; and 2) an undercut formed in said inner cannula at a proximal end of said biopsy reservoir so as to define a second finger, said second finger configured so as to inhibit movement of the tissue sample proximally into the lumen of said inner cannula when suction is applied to said inner cannula; and f) wherein moving said outer cannula from the distal position to the proximal position thereof and creating suction at the biopsy reservoir causes a tissue sample to be pulled into the biopsy reservoir and wherein moving said outer cannula from the proximal position to the distal position thereof causes the cutter to cut the tissue sample from surrounding tissue and also captures the tissue sample within the biopsy reservoir.

20. The needle biopsy device as recited in claim 19, wherein said first and second fingers define generally pointed members.

21. The needle biopsy device as recited in claim 19, wherein said first and second fingers are bent inwardly so as to partially obscure the lumen of the inner cannula and thus further inhibit movement of the tissue sample out of the biopsy reservoir.

22. A needle biopsy device comprising:

a) a suction source;

b) an inner cannula having a biopsy reservoir formed proximal a distal end thereof, and also having a lumen formed therein, said lumen providing fluid communication between the suction source and the biopsy reservoir;

c) an outer cannula slidably disposed about said inner cannula, said outer cannula having a cutter formed at a distal end thereof, said outer cannula having a distal position substantially covering the biopsy reservoir of said inner cannula and having a proximal position substantially exposing the biopsy reservoir of said inner cannula;

d) an actuating mechanism for moving said outer cannula from the distal position to the proximal position thereof, for facilitating the application of suction from said suction source to the biopsy reservoir, and for moving said outer cannula from the proximal position to the distal position thereof;

e) a vanity shield substantially covering said actuating mechanism so as to enhance aesthetic appeal; and f) wherein moving said outer cannula from the distal position to the proximal position thereof and creating suction at the biopsy reservoir causes a tissue sample to be pulled into the biopsy reservoir and wherein moving said outer cannula from the proximal position to the distal position thereof causes the cutter to cut the tissue sample from surrounding tissue and also captures the tissue sample within the biopsy reservoir.

* * * * *